United States Patent [19]

Figgie, III

[11] Patent Number: 4,650,490

[45] Date of Patent: Mar. 17, 1987

[54] SURGICAL IMPLANT PROCESS FOR A PROSTHETIC KNEE

[75] Inventor: Harry E. Figgie, III, Pepper Pike, Ohio

[73] Assignee: Figgie International Inc., Willoughby, Ohio

[21] Appl. No.: 693,131

[22] Filed: Jan. 22, 1985

[51] Int. Cl.$^4$ ................................................. A61F 2/38
[52] U.S. Cl. ......................................................... 623/20
[58] Field of Search ................ 128/92 C; 3/1.9, 1.91, 3/1.911; 623/20, 21, 22, 23, 16

[56] References Cited

U.S. PATENT DOCUMENTS 4,209,861  7/1980  Walker et al. ...................... 3/1.911
4,298,992  11/1981  Burstein ................................. 3/1.911
4,470,158  9/1984  Pappas et al. ......................... 3/1.911

Primary Examiner—Richard J. Apley
Assistant Examiner—David J. Isabella
Attorney, Agent, or Firm—Regan J. Fay

[57] ABSTRACT

A method of surgically implanting a human knee prosthesis is provided where (i) the postoperative ratio of the adjusted patellar tendon length to the prosthetic patellar height (APL/PH') is from about 1.2 to about 0.9; and (ii) the tibial component of the knee prosthesis is implanted so that the postoperative anterior/posterior center line of the tibial component is located posterior with respect to the preoperative anterior/posterior center line of the tibial plateau by an amount equal to or greater than about 5% of the anterior/posterior distance of the tibial plateau. An implanted prosthetic human knee joint is also provided having either or both the normalized APL/PH' ratio or the 5% posterior placement.

8 Claims, 3 Drawing Figures

POST-OPERATIVE

PRE-OPERATIVE

POST-OPERATIVE

SURGICAL IMPLANT PROCESS FOR A PROSTHETIC KNEE

FIELD OF INVENTION

The present invention relates to an implanted prosthetic human knee joint and a method of surgically implanting a total knee joint prosthesis having femoral, tibial, and patellar components.

BACKGROUND OF INVENTION

Despite patellar resurfacing, symptoms referable to the patella femoral joint are still a major reason for complaints after total knee arthroplasty. Up to 40% of patients undergoing total knee arthroplasty have anterior knee or retropatellar pain in the postoperative period. Reoperation for patella femoral symptoms constitutes a large percentage of revisions of total knee arthroplasties. Despite the magnitude of this problem no correlation has been made with knee function or implant position. Most studies have dealt only with major technical errors that have led to patella fracture, lateral subluxation or dislocation of the patella. Patellar fractures following wide lateral retinacular release and/or massive patellar resection may in part be related to a vascular insult. Patellar subluxation, abnormal tracking or dislocation is most often associated with inadequate balance or rotational malalignment of the tibial component. These problems, however, account for only a small percentage of all patella femoral complaints and are not as widespread as the vague, aching pain or mechanical symptoms that are most commonly identified in the postoperative period.

The focus in total knee arthroplasty is to insure correct rotational, anterior/posterior and varus/valgus positioning of the implant as well as to insure soft tissue balance. Anterior/posterior and varus/valgus stability are the primary concerns. Only after all components are positioned can one check the position of the patella. However, there are several technical errors in an otherwise technically well aligned prosthesis that can lead to poor balance of the patella femoral joint. First, the choice of femoral component that is either too small in the anterior/posterior position or alternately too anteriorly placed will result in a large flexion gap. To balance this gap in extension an excess of distal femur must be removed.

These gaps are usually filled with a thick tibial component. This results in a functional shortening of the patellar ligament with its attendant increase in symptoms as discovered herein. Other theoretical technical errors include a relative medial position of the tibial and femoral components or lateral positioning of the patellar component which could increase the lateral patellar pressure syndrome. If the patella subluxes laterally or if the patella femoral pressure is too great a surgeon has very few options. The first is a lateral retinacular release. The lateral release has its own problems as well as being a relatively poor solution for an iatrogenic shortening or lengthening of the patellar ligament. Another alternative is lateralization of the components of the total knee arthroplasty. While this is attractive from a patellar femoral tracking standpoint, it will increase the varus moment during single leg stance. There is no data discussing potential benefits from lateralization or risks of aseptic loosening from an asymmetric positioning of the prosthesis. The final alternative is a major distal realignment including elevating or transferring the tibial tubercle or Z-lengthening of the patellar ligament. A bony procedure places the fixation of the tibial component at risk and lengthening puts the ligament at risk. Both may slow the rehabilitative procedure substantially.

SUMMARY OF INVENTION

A study of consecutive posterior stabilized condylar knee arthroplasty identified several significant problems of the patellar femoral joint. Critical analysis of the tibiopatella-femoral mechanical axis identified two variables that were found to markedly impact upon the functional result of the prosthesis: (1) the ratio of adjusted patellar ligament length to prosthetic patellar height (APL/PH') and (2) posterior placement of the tibial prosthesis with respect to the center line of the tibial plateau as viewed in a lateral radiograph. When adjusted for changes in tibial plateau height, knees with patella alta (APL/PH' greater than 1.2) or patella infera (APL/PH' less than 0.9) were found to have statistically significant losses in quantitative knee score (Modified Mayo Clinic) and range of motion and increases in severe patellar femoral pain and mechanical symptoms requiring surgical revision. Placement of the tibial prosthesis posteriorly on the tibial plateau by an amount equal to at least 5% of the total anterior/posterior distance of the tibia plateau (usually 3 to 5 mm) gave statistically significant improvement in functional result.

The present invention is directed to an implanted prosthetic human knee joint and a method of surgically implanting a human knee prosthesis. A knee prosthesis having femoral, tibial and patellar components is provided. The preoperative ratio of the patellar tendon length (PT) to the patellar height (PH) is determined. Tibial and femoral portions are surgically removed so that the postoperative ratio of the adjusted patellar tendon length to the prosthetic patellar height (APL/PH') is from about 1.2 to about 0.9. The femoral, tibial and patellar components are implanted. The tibial component of the knee prosthesis is implanted so that its postoperative anterior/posterior center line is located posterior to the preoperative anterior/posterior center line of the tibial plateau. The tibial component is located to the posterior of the preoperative center line as viewed in the lateral radiograph by an amount equal to or greater than about 5% of the anterior/posterior distance of the tibial plateau as viewed in a lateral radiograph. Either normalizing the APL/PH' ratio or 5% posterior placement can be used in accordance with the present invention, use of both features being especially preferred.

The results pursuant to the present invention show that those prosthetic knees having a normal APL/PH' ratio and a posteriorly located tibial prosthetic component had quantitative scores that averaged 97 and all had good or excellent results. Results in accordance with the present invention show that maintaining the APL/PH' ratio between about 0.9 to about 1.2 and placing the tibial prosthesis posterior with respect to the tibial plateau centroid by an amount equal to or greater than 5% of the anterior/posterior tibial plateau distance will minimize significant patella femoral symptoms and improve functional operation of the knee prosthesis. Either normalizing the APL/PH' ratio or 5% posterior placement results in reduced patella femoral symptoms and improved knee operation in accordance with the present invention, use of both features offering even greater results than one feature alone.

DESCRIPTION OF PREFERRED EMBODIMENT

Surgical Study

Figure 1:
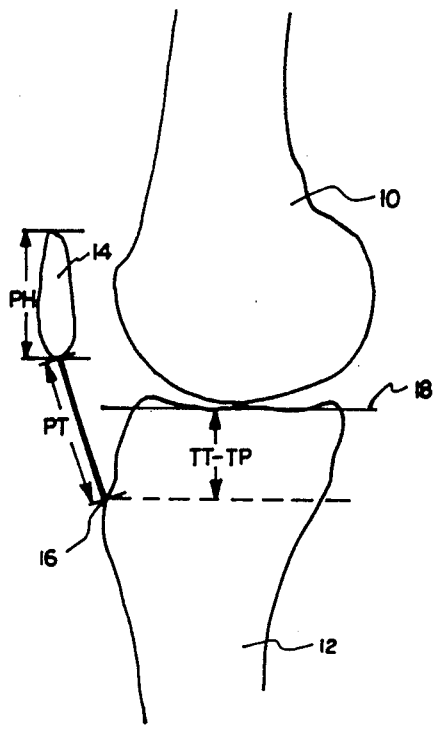
FIG. 1 is a schematic drawing of a lateral radiograph of a preoperative human knee.

The present invention results from a study of consecutive posterior stabilized condylar knee arthroplasty. Three significant problems of the patella femoral joint were identified: mechanical symptoms not impairing function, mechanical symptoms causing decreased function, and pain. Asymptomatic clicking of the prosthesis in terminal extension, or painless crepitation throughout the range of motion usually does not impair function. Symptomatic mechanical findings include extensor lag, giving way, patellar subluxation or painful locking. Pain syndromes ranged from mild anterior knee or retropatellar ache following heavy activity to severe, often disabling retropatellar pain through the midrange of flexion that decreases function. Prolonged sitting, arising from a sitting position, descending stairs and often even walking on level surfaces may be limited when pain or mechanical symptoms are present. An analysis of these problems demonstrated that altering the normal tibia patella-femoral mechanical axis and maintaining the APL/PH' ratio in the range from about 0.9 to about 1.2 significantly affected these problems and the ultimate outcome of the arthroplasty.

Knee function and patella femoral symptoms were correlated with implant position in 116 consecutive posterior stabilized condylar knee arthroplasties implanted in 101 consecutive patients. Seventy patients were female and 31 were male. All patients were followed for a minimum of two years and a maximum of five years. Average follow-up was 3.5 years. Fifty-nine were left knees and 57 were right knees. The underlying diagnosis was osteoarthritis or post-traumatic arthritis in 74 knees, rheumatoid arthritis in 31 knees, ankylosing spondylitis in one knee. The prosthesis was used for revision of existing failures of previous arthroplasties in 11 knees. All patients were evaluated using the Modified Mayo Clinic Knee Score in which 100 points is the maximum score. The score is defined by the patient's pain, function, stability, and range of motion. All patients were followed prospectively by sequential history, physical examination and radiographic evaluation. Specific questions regarding mechanical functioning and pain related to the patella femoral joints were asked. The questions concerned pain after prolonged sitting, arising from the sitting position, descending stairs, walking on level surfaces, extensor lag, giving way, patellar subluxation, painful locking or catching, clicking of the prosthesis in terminal flexion or extension or crepitation with or without pain throughout the range of motion. The patients were also asked if they had other pain that was vague in nature that could not be related to either the joint line or to the patella femoral joint. Most patients were quite specific with regard to the character and extent of the pain and as to whether or not the mechanical or pain complaints decreased function.

Radiographic Evaluation

Standing anterior posterior and lateral radiographs were evaluated for position of the implants. This included the presence or absence of lucent lines, varus/valgus alignment and anterior/posterior position of the implant. Measurements for the relative position of the patellar ligament, patella and relationship of the tibial plateau to the tibial tubercle were taken on both preoperative (FIG. 1) and postoperative lateral radiographs (FIG. 2). The terms "patellar ligament" and "patellar tendon" are used interchangeably herein.

Figure 2:
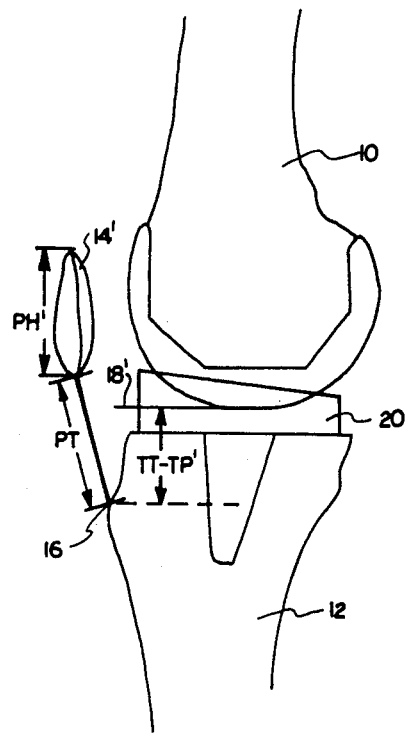
FIG. 2 is a schematic drawing of a lateral radiograph of a postoperative total knee prosthesis.

FIG. 1 represents a schematic drawing of a lateral radiograph of a preoperative human knee. The inferior or distal end of a femur 10 is schematically shown in relationship to the superior or proximal end of a tibia 12. The patella or kneecap is designated 14.

The following measurements were obtained from the preoperative lateral radiographs (FIG. 1). The first measurement was the overal length PH of the patella 14 measured from the inferior pole to the superior pole. The second measurement was the length of the patellar tendon (PT) taken from the inferior pole of the patella 14 to the tibial tubercle 16. The third measurement was the tibial plateau height (TT-TP) which was measured as a perpendicular distance from a horizontal line through the tibial tubercle 16 to a line representing the weight-bearing surface 18 of the tibial plateau. From these measurements the diagnosis of preoperative patella alta, patella infera or normal position was made. That diagnosis depends on the ratio of the patellar tendon length PT to the patellar height PH.

FIG. 2 represents a schematic of a lateral radiograph of a postoperative total knee. The measurements that were taken were similar to those described in FIG. 1, with certain numbers and letters in prime to indicate prosthetic distances or parts. The patellar height PH' was measured from the inferior pole of the prosthetic patella 14' to the superior pole of the prosthetic patella 14'. The patellar tendon length PT was measured from the tibial tubercle 16 to the inferior pole of the prosthetic patella 14'. The postoperative tibial plateau height TT−TP' was measured from the tibial tubercle 16 to the weight-bearing surface 18' of the tibial prosthetic component. To the extent that this height was different from the preoperative distance TT−TP a relative lengthening or shortening of the patellar tendon PT would be noted.

In most cases the inferior pole of the prosthetic patella 14' coincided with the inferior pole of the bony patella 14. As a control for magnification the distance from the tibial tubercle 16 to the inferior pole of the bony patella 14 was also measured on the postoperative radiographs. All ratios of the measurement of the distance from the inferior pole of the bony patella 14 to the tibial tubercle 16 on the pre- and postoperative films fell within 97 to 103% and, therefore, the pre- and postoperative radiographs were treated as being essentially identical.

The adjusted patellar tendon length APL was calculated by subtracting the difference between the postoperative and preoperative tibial plateau heights from the postoperative patellar tendon length:

$$APL = PT_{Post} - [(TT - TP') - (TT - TP)]$$

This calculation considers the change in the functional length of the patellar tendon.

The calculation of the adjusted functional patellar tendon length APL is based on several assumptions: first, that the preoperative and postoperative radiographs are essentially the same and, second, that the included angle between the patellar tendon and an intersecting line parallel to the tibial plateau height is negligible. The pre- and postoperative radiographs are virtually identical as discussed earlier. The included angle measured 7 to 12 degrees and the variance between pre- and postoperative angles was never more than 5 degrees. Such a variance was felt to have only a negligible effect on the overall results. Accordingly, both assumptions were deemed valid.

From the measurements obtained from the preoperative and postoperative lateral radiographs (FIGS. 1 and 2), the ratio of the adjusted patellar tendon length APL to the postoperative prosthetic patellar height PH' can be obtained. (Prior to the present invention the normal range of the PT/PH ratio for a human knee had been defined as being in the range of 0.9 to 1.2.) For the present invention the normal range of the prosthetic knee after implant is where the APL/PH' ratio is greater than or equal to about 0.9 and less than or equal to 1.2. Two abnormal groups have been identified: patella alta where the APL/PH' ratio is greater than 1.2 and patella infera where the APL/PH' ratio is less than about 0.9.

Figure 3:
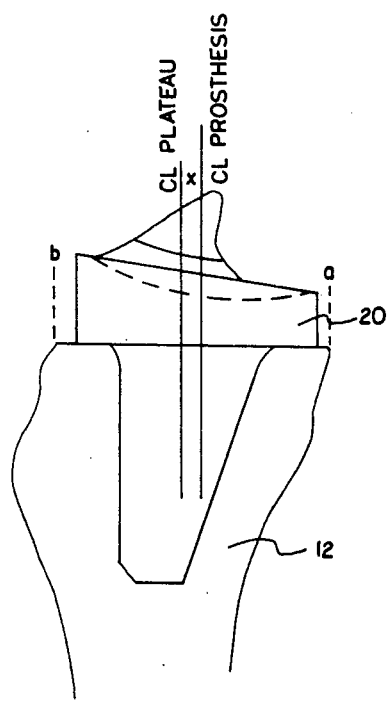
FIG. 3 is a schematic drawing of a lateral radiograph showing a postoperative tibial plateau having a tibial implant component.

A second feature of the present invention is the location of the center line of the tibial component 20 of the knee prosthesis. The position of the tibial component 20 with respect to the center line of the tibial plateau in a lateral radiograph was obtained from the postoperative lateral radiographs (see FIG. 3). FIG. 3 represents a schematic drawing of a lateral radiograph showing the postoperative tibial plateau. The preoperative anterior/posterior center line CL plateau represents the center line (as viewed anterior/posterior) or centroid of the tibial plateau. The postoperative anterior/posterior center line of the tibial component 20 is designated CL prosthesis. The distance X between CL plateau and CL prosthesis represents the distance that the center line of the prosthesis was located posterior to the center line of the tibial plateau. The anterior/posterior distance of the tibial plateau is the distance between the anterior cortex b of the tibial plateau to the posterior cortex a of the tibial plateau. One feature of the present invention is that the distance X is equal to or greater than 5% of the anterior/posterior distance of the tibial plateau; in that manner, the prosthesis will be adequately posteriorly placed. In the preferred form, the difference between the anterior cortex b of the tibial plateau and the anterior surface of the prosthesis plus the distance from the posterior surface of the prosthesis to the posterior cortex a of the tibial plateau should be equal to the distance X—i.e., the posterior displacement distance of the tibial component from the center line of the tibial plateau.

For purposes of analysis, the distance the tibial component of the prosthesis was positioned either anterior or posterior to the center line of the tibial plateau was divided by the overall anterior/posterior distance of the tibial plateau. This standardized the calculation of all prostheses and all sizes of tibias.

Surgical Process And Implanted Joint

The method according to the present invention of surgically implanting a human knee prosthesis comprises several steps. First, a total knee prosthesis is provided having a femoral component, a tibial component, and a patellar component. A variety of different types of total knee prostheses may be used in the surgical implant method of the present invention. One prosthesis which is particularly preferred is termed the Burstein Knee which is disclosed in U.S. Pat. No. 4,298,992.

Second, the preoperative ratio of the patellar tendon length to the patella height is determined. Next, tibial and/or femoral portions are surgically removed so that the postoperative ratio of the adjusted patellar tendon length APL to the prosthetic patella height PH' is from about 1.2 to about 0.9. If preoperative patella alta is diagnosed, more of the distal end of the femur is removed and less of the proximal end of the tibia is removed. If patella infera is diagnosed, then more of the proximal end of the tibia is removed and less of the distal end of the femur is removed. The amounts of tibia and femur to be removed depend on a variety of factors including the extent of patella alta or infera and the size of the prosthesis. The size of the tibia and femur resections are within the skill of a surgeon considering the foregoing factors and the objects of the present invention.

The surgical method of the present invention does not change the actual length of the patellar ligament or tendon PT. However, changing the tibial plateau height or, in other words, changing the knee joint surface relative to the hip changes the mechanical advantage or functional effective length of the patellar ligament. If the tibia plateau height is increased, the knee joint surface moves closer to the hip. That results in functional shortening of the patellar ligament. Functional lengthening is desired for patella infera. In either patella alta or infera, the proper postoperative level of the prosthetic knee joint should put the adjusted patellar ligament to patellar height ratio within the normal range.

The tibial component of the knee prosthesis is implanted so that its postoperative anterior/posterior center line is located posterior with respect to the preoperative interior/posterior center line of the tibial plateau by an amount equal to or greater than about 5% of the anterior/posterior distance of the tibial plateau.

The femoral and patellar components are also implanted, and the knee prosthesis implant is otherwise performed in accordance with normal surgical techniques.

The present invention also contemplates the implanted prosthetic joint in the human patient. Either the normalized APL/PH' ratio feature or the 5% posterior placement feature of the present invention can be used in the final implanted joint. The preferred implanted joint uses both features.

Results

The anterior/posterior positioning of the tibial component and the effect of the relative lengthening or shortening of the patellar ligament was analyzed with respect to functional results in the patient study. The patients were categorized according to patella alta, normal patella and patella infera. Each of these categories was correlated with quantitative knee score, range of motion, specific patella femoral pain, other pain specifically not patella femoral, and mechanical symptoms of the patella femoral joint. Surgical revision rates for each group were also calculated. These results were compared statistically to the findings within the normal range. The relative anterior posterior position of the prosthesis with respect to the center line of the tibial plateau and its effect on function was noted on each of the three APL/PH' groups. These results are also reported below.

Statistical analysis was performed in comparing all of the three groups. All statistics were performed using the students t test.

sion for aseptic loosening. This group tended to be unhappy with overal functional level (Table I).

Patella Infera.

Forty-three knees had patella infera postoperative (APL/PH' less than 0.9). The functional and quantitative knee score averaged 86, which was statistically different when compared with the normal group. Knee motion averaged 99 degrees which is 9 degrees less than the normal group. Eighteen knees (42%) had patella femoral pain and it was disabling in seven (17%). Symptomatic mechanical complaints of painful cracking,

TABLE I

SUMMARY OF FUNCTIONAL RESULTS AND ADJUSTED PATELLAR TENDON/PATELLAR HEIGHT RATIOS

| N | Class | Knee Score | Range of Motion | Patella-Femoral Pain (%) | | Patella-Femoral Mechanical Symptoms (%) | | | Other Pain Not Patella-Femoral (%) | Patellar Revision (%) | Total Knee Revision for Aseptic Loosening (%) | Manipulation (%) |
|---|---|---|---|---|---|---|---|---|---|---|---|---|
| | | | | Mild | Severe | Asymptomatic | Mild | Severe | | | | |
| 8 | Alta APL/PH' > 1.2 | 83 | 102° | 0 | 50 | 25 | 0 | 25 | 38 | 13 | 13 | 0 |
| 65 | Normal 1.2 ≧ APL/PH' ≧ 0.9 | 96 | 108° | 1.5 | 1.5 | 12 | 2 | 0 | 20 | 0 | 0 | 9 |
| 43 | Infera APL/PH' < 0.9 | 86 | 99° | 25 | 17 | 15 | 17 | 25 | 17 | 17 | 0 | 22 |

(A) Statistically significant difference from normal at P ≦ 0.01 for all categories except for range of motion.
(B) Statistically significant difference from normal at P ≦ 0.05 for range of motion.

The APL/PH' Ratio

Normal.

There were 65 knees in the normal APL/PH' group. These knees had an average quantitative score of 96 and an average range of motion of 108 degrees and two of 65 knees (3%) had patellar pain. One of these knees had mild pain and weakness on standing. The other patient had severe pain and mechanical symptoms from a rotary malalignment of the tibia which led to lateral tracking of the patella. Eight of 65 knees (12%) had asymptomatic crepitation that did not alter function and 13 of 65 knees (20%) had mild nonpatella femoral pain. Within this group there were no revisions for patella femoral complaints other than the above-mentioned patient who had a tibial component malalignment. There was no case of revision for aseptic loosening in this group. Six patients in this group (9%) required manipulation in the postoperative period.

Patella Alta.

There were eight knees in the group that had patella alta postoperative (APL/PH' greater than 1.2). Knee function was decreased in a statistically significant manner when compared to the normal APL/PH' group. Quantitative knee scores averaged 83. Severe patella femoral pain occurred in four of eight knees and severe patella femoral mechanical symptoms occurred in two of eight knees. Three knees had vague, nonpatella femoral pain causing lowered functional results. One knee required revision of the patella for severe symptoms. The range of motion in this group averaged 102 degrees, which was 6 degrees less than the normal group. No knees in this group required manipulation postoperatively. One additional knee in this group required revijumping or catching were present in 18 knees (42%) and 10 (25%) felt it was functionally disabling. Five knees in this group had revision of the patella femoral joint. One underwent a patellectomy. One patient was awaiting revision as he could ambulate only in a long-leg brace locked in extension. In this group the overall revision rate was 7 of 43 or 17%. Nine knees (22%) required manipulation in the postoperative period. No knees in this group underwent revision for aseptic loosening. Overall, this group had marked decrease in function compared to normal and the patients with the more severe knee symptoms were extremely dissatisfied. (Table I).

As discussed in more detail below, surgical removal of femoral and tibial portions to insure a normal APL/PH' ratio results in statistically better results compared to patella alta and patella infera. The results of Table I show that there is a statistically significant decrease in knee function when the APL/PH' ratio lies outside of the 1.2 to 0.9 range. When this occurs, knee scores and range of motion are statistically significantly diminished. In addition there is a statistically significant increase in severe patella-femoral pain, mechanical symptoms and patellar revision.

Revision of the prosthesis for aseptic loosening was statistically significantly higher in the alta but not the infera groups. Manipulation was necessary more frequently in those patients with infera than normal but it was not required in patients with alta.

In summary, iatrogenic patella alta and infera are to be avoided as they may seriously compromise the overall results. Patella alta and infera can be avoided in accordance with the present invention by surgically removing proper amounts of the femur and tibia during the knee prosthesis implant.

TABLE II

ANALYSIS OF ANTERIOR-POSTERIOR POSITION OF THE TIBIAL COMPONENT AND FUNCTIONAL RESULTS

| | Severe-Patella-Femoral Symptoms | All Symptomatic Patella-Femoral |
|---|---|---|

TABLE II-continued

ANALYSIS OF ANTERIOR-POSTERIOR POSITION
OF THE TIBIAL COMPONENT AND FUNCTIONAL RESULTS

| Class | N T < 5% | N T ≧ 5% | Knee Score T < 5% | Knee Score T ≧ 5% | (%) T < 5% | (%) T ≧ 5% | Complaints (%) T < 5% | Complaints (%) T ≧ 5% |
|---|---|---|---|---|---|---|---|---|
| Alta APL/ PH' > 1.2 | 4 | 4 | 78 AC | 90 BC | 75 AC | 0 | 75 AD | 50 AD |
| Normal 1.2 ≧ APL/ PH' ≧ 0.9 | 40 | 25 | 93 B | 97 | 0 | 0 | 13 A | 4 |
| Infera APL/ PH' < 0.9 | 36 | 7 | 84 AC | 90 BC | 20 AC | 0 | 47 AC | 14 AC |

| Class | Other Pain (%) T < 5% | Other Pain (%) T ≧ 5% | Patella Revision (%) T < 5% | Patella Revision (%) T ≧ 5% | Good Knees With Good or Excellent Results (%) T < 5% | Good Knees With Good or Excellent Results (%) T ≧ 5% |
|---|---|---|---|---|---|---|
| Alta APL/ PH' > 1.2 | 75 AC | 0 C | 25 AC | 0 C | 50 AC | 100 C |
| Normal 1.2 ≧ APL/ PH' ≧ 0.9 | 29 AC | 8 | 0 | 0 | 97 | 100 |
| Infera APL/ PH' < 0.9 | 20 AC | 0 C | 20 AC | 0 C | 70 AC | 100 C |

T < 5%: Anterior Positioning
T ≧ 5%: Posterior Positioning
(A) Statistically significant difference (at P ≦ 0.01) from a normal (1.2 ≧ APL/PH' ≧ 0.9) knee with tibial component seat ≧ 5% of tibial plateau posterior to the tibial centroid.
(B) Identical to A but P ≦ 0.05.
(C) Statistically significant difference at P ≦ 0.01 within its own class (e.g. infera to infera).
(D) Same as C with P ≦ 0.05.

Posterior Position of the Tibial Prosthesis

The analysis summarized in Table II shows that posterior placement of the tibial prosthesis from the preoperative anterior/posterior tibial center line or tibia centroid by a distance equal to or greater than 5% of the overall anterior/posterior tibial distance gave statistically significant improvement in function over those knees where the prostheses were more anteriorly placed. The choice of a percentage rather than a fixed distance allows standardization for variations in tibial size and configuration. Despite posterior placement, however, those knees with patella alta or patella infera continued to have functionally poorer results than those knees with normally maintained APL/PH' ratios. See the foregoing discussions of the results set forth in Table I and the importance in accordance with the present invention of surgically removing bone portions to insure a normal APL/PH' ratio. Within the group of 25 knees that had both a normal APL/PH' ratio and a tibial component posteriorly placed, knee scores averaged 97 and the range of motion averaged 110 degrees. There were no symptomatic patella femoral joints and no patella femoral revisions. Two knees (8%) had vague knee pain specifically not patella femoral. There were no revisions for aseptic loosening in this group. All 25 of the knees in this group had good or excellent results and the patients were uniformly satisfied.

In the knees with postoperative patella alta, posterior placement of the prosthesis did give functional benefits. In these four knees the knee score averaged 90. Although none had severe pain, two of four knees (50%) continued to have mild patella femoral mechanical symptoms. There were no revisions of the patella femoral joint, no revisions in the group for aseptic loosening, and no knees in this group were manipulated. All four of the knees in this group rated good or excellent results.

In the knees with postoperative patella infera, posterior positioning of the prosthesis again offers protective benefits. In these seven knees scores averaged 90. No knees had severe mechanical symptoms but one (14%) continued to have severe patella femoral pain lowering functional score. However, there were no cases of revision of patella femoral joint and no cases of revision for aseptic loosening. All seven knees in this group rated good or excellent results.

Relative anterior positioning of the tibial component in a knee that has postoperative patella alta or patella infera will result in consistently inferior functional results. In those four knees with patella alta and anterior positioning of the tibial prosthesis, knee scores averaged 78. Three of four (75%) had severe patella femoral pain and mechanical symptoms. Three knees (75%) had nonpatella femoral aching pain. One patient (25%) in this group required patellar revision and one patient in this group required revision for aseptic loosening. No patients in this group required postoperative manipulation. Only two of the knees (50%) rated good or excellent results. The sample results are statistically significantly inferior to the control group in all cases.

In knees with patella infera and relative anterior positioning of the tibial prosthesis the results again are inferior to the control. In these 36 knees, scores averaged 84. Seven of 36 knees (20%) had severe patella femoral mechanical symptoms. Seven knees had vague, nonpatella femoral pain and five knees in the group underwent patella femoral revision with a sixth requiring a patellectomy. A seventh patient with a single knee is awaiting revision. This is a revision rate of seven of 36 knees or 20%. No knees were revised for aseptic loosening. Twenty-five knees (70%) in this group rated either good or excellent results. Again, this group tended to have a very poor satisfaction rate and patients that fell out of the good or excellent range in general tended to be quite dissatisfied with their overall functional level.

Posterior positioning of the tibial prosthesis is seen to have a beneficial effect. While it cannot fully correct for abnormalities in APL/PH' ratios, it does offer some protective benefits. The Wilcoxson Sign Rank Test supports the overall difference between posterior and anterior positioning of the implant. It shows a statistically signficant difference between function of anterior and posterior position at P less than or equal to 0.01.

In each case posterior positioning of the implant gave better results than anterior positioning. As noted in Table I, maintenance of the APL/PH' ratio between 1.2 and 0.9 is important. The results in Table II indicate that the combination of posterior implant position and an APL/PH' ratio between 1.2 and 0.9 give consistently excellent results.

Surgical Procedure and Implant Evaluation

The results of the present invention show statistically signficant functional gains from proper positioning of the patella femoral mechanical axis. The ideal position places the anterior/posterior center line of the tibial prosthesis posterior to the anterior/posterior center line or centroid of the tibial plateau by an amount equal to or greater than 5% of the anterior/posterior distance of the tibial plateau (usually 3 to 5 mm) and places the APL/PH' ratio between 1.2 and 0.9. In this normal group the results were uniformly good or excellent and all patients were satisfied with their overall results. In knees where the prosthesis was posteriorly placed but the APL/PH' ratio was outside the normal range the patients had generally successful results but not as good as those with the APL/PH' ratio lying within the normal range.

Vague, nonpatellar pain in anteriorly positioned protheses especially with the APL/PH' ratio outside of the normal range is shown in Table II. This pain may be related to capsular stretching, and it occurs due to an imbalance in the position of the prosthetic knee joint with respect to the preoperative joint line position. Furthermore, vague aches in the hamstrings and quadriceps were more frequent in the improperly aligned protheses than in normals. This variety of vague complaints in addition to the specific patella femoral complaints is worse in those patients when the APL/PH' ratio is out of the normal range and does contribute to both loss in functional results and patient satisfaction.

It appears the best solution for patellar problems is prevention, since those patients who develop problems appear to be segregated in several reasonably discrete categories. A thorough preoperative evaluation and planning should be made including radiographic evaluation of the patellar tendon and the patellar tendon to patellar height ratio. Care must be taken to avoid making a thin tibial plateau cut and a relatively thick distal femoral extension cut and thus using a thick tibial component to restore extension balance. This will result in a relative shortening of the patellar ligament and may lead to severe postoperative symptoms. When preoperative radiographs indicate patella alta then bone should be preferentially removed from the distal femur and a thicker tibial component should be used. This will move the weight bearing center of the knee further proximally and therefore relatively shorten the patellar ligament. The ultimate level of the prosthetic knee joint should put the adjusted patellar ligament to patellar height length ratio within the normal range.

Maximum posterior placement of the tibial component as is consistent with good tibial fixation is beneficial in reducing patella-femoral complaints. This technique tends to move the center of rotation of the knee to a relatively posterior position. This should decrease the forces and contact stresses acting on the patella.

Further benefits may be inferred from the posterior positioning. Placement of the central peg along the posterior tibial cortical wall minimizes stress concentration and benefits patella-femoral contact stresses. It also may prolong the implant life.

There are several technical considerations that may limit the maximum amount of posterior positioning. First, it is beneficial to use the largest possible prosthetic tibial plateau in order to spread the applied load over the maximum area and therefore decrease the unit load across the implant/cement/bone interfaces. As a result, it may be impossible to adequately seat the prosthesis posteriorly due to potential overhang of the prosthesis into the popliteal space. Second, the configuration of the proximal tibia is highly variable. The posterior cortex limits the maximum posterior displacement due to its interference with the central fixation peg.

One important feature for minimizing patella-femoral complaints is to normalize the APL/PH' ratio. This may be accomplished by the availability of custom fit components or several thicknesses of femoral as well as tibial components to allow for more close modeling of the knee. Alternatively, one must be prepared to bone graft to make up significant bone stock losses or errors in cutting. Preoperative roentgenograms should be analyzed carefully for evidence of patella alta or infera. Patella femoral contact forces can be minimized by a relatively posteriorly positioning of the tibial prosthesis on the tibial plateau and normalization of the APL/PH' ratio. In cases where there is a significant femoral bone stock loss or marked patella infera, a custom fit femoral prosthesis or bone graft to allow a normalization of the patella femoral joint in the prosthetic knee is recommended.

What is claimed is:

1. A method of surgically implanting a human knee prosthesis comprising:
    providing a knee prosthesis having a femoral component, a tibial component and a patellar component,
    determining the preoperative ratio of the patellar tendon length to the patellar height,
    surgically removing bone portion of either or both the tibia and the femur so that the postoperative ratio of the adjusted patellar tendon length to the prosthetic patellar height is from about 1.2 to about 0.9,
    implanting the femoral component of the knee prosthesis,
    implanting the tibial component of the knee prosthesis so that the postoperative anterior/posterior center line of the tibial component is located posterior with respect to the preoperative anterior/posterior center line of the tibial plateau by an amount equal to or greater than about 5% of the anterior/posterior distance of the tibial plateau, and
    implanting the patellar component of the knee prosthesis.

2. A method of surgically implanting a human knee prosthesis as claimed in claim 1 wherein the adjusted patellar tendon length equals the postoperative patellar tendon length less the difference between the postoperative and preoperative tibial plateau heights.

3. A method of surgically implanting a human knee prosthesis as claimed in claim 2 wherein the knee prothesis is a total condylar knee prothesis.

4. A method of surgically implanting a human knee prosthesis as claimed in claim 1 wherein the amount of posterior placement of the tibial component equals the sum of the distance between the anterior cortex of the tibial plateau and the anterior surface of the tibial component plus the distance between the posterior surface of the tibial component and the posterior cortex of the tibial plateau.

5. In a method of surgically implanting a human knee prosthesis wherein the knee prosthesis has a femoral component, a tibial component and a patellar component, the improvement comprising:

surgically removing bone portion of either or both the tibia and the femur so that the postoperative ratio of the adjusted patellar tendon length to the prosthetic patellar height is from about 1.2 to about 0.9, and implanting the tibial component of the knee prosthesis so that the postoperative anterior/posterior center line of the tibial component is located posterior with respect to the preoperative anterior/posterior center line of the tibia plateau by an amount equal to or greater than about 5% of the anterior/posterior distance of the tibial plateau.

6. A method of surgically implanting a human knee prosthesis as claimed in claim 5 wherein the adjusted patellar tendon length equals the postoperative patellar tendon length less the difference between the postoperative and preoperative tibial plateau heights.

7. A method of surgically implanting a human knee prosthesis as claimed in claim 6 wherein the knee prothesis is a total condylar knee prothesis.

8. A method of surgically implanting a human knee prosthesis as claimed in claim 5 wherein the amount of posterior placement of the tibial component equals the sum of the distance between the anterior cortex of the tibial plateau and the anterior surface of the tibial component plus the distance between the posterior surface of the tibial component and the posterior cortex of the tibial plateau.

* * * * *